(12) United States Patent
Omori (10) Patent No.: US 8,197,655 B2
(45) Date of Patent: Jun. 12, 2012

(54) SYSTEM AND METHOD FOR DETECTING INTERACTION BETWEEN SUBSTANCES BY SUPERIMPOSINGLY APPLYING SINUSOIDAL VOLTAGE

(75) Inventor: Shinji Omori, Tokyo (JP)

(73) Assignee: Sony Corporation, Tokyo (JP)

( * ) Notice: Subject to any disclaimer, the term of this patent is extended or adjusted under 35 U.S.C. 154(b) by 1339 days.

(21) Appl. No.: 11/385,961

(22) Filed: Mar. 22, 2006

(65) Prior Publication Data

US 2006/0226028 A1 Oct. 12, 2006

(30) Foreign Application Priority Data

Mar. 31, 2005 (JP) ................................. 2005-102121

(51) Int. Cl.
*B01D 57/02* (2006.01)
(52) U.S. Cl. .................. 204/547; 204/406; 204/643
(58) Field of Classification Search ................. 204/643, 204/450–471, 546–550, 600–621; 435/461, 435/470, 173.6, 285.2
See application file for complete search history.

(56) References Cited

U.S. PATENT DOCUMENTS

| | | | | |
|---|---|---|---|---|
| 3,622,485 | A * | 11/1971 | Preece et al. | 204/477 |
| 4,187,160 | A * | 2/1980 | Zimmermann | 359/296 |
| 6,113,768 | A * | 9/2000 | Fuhr et al. | 204/643 |
| 2001/0036095 | A1* | 11/2001 | Ooike et al. | 363/84 |
| 2003/0006140 | A1* | 1/2003 | Vacca et al. | 204/547 |
| 2004/0112748 | A1* | 6/2004 | Lee et al. | 204/547 |

FOREIGN PATENT DOCUMENTS

| | | |
|---|---|---|
| JP | 2002-541823 | 12/2002 |
| JP | 2004-135512 | 5/2004 |
| JP | 2004-524823 | 8/2004 |

OTHER PUBLICATIONS

Serway, R. A. Physics for Scientists and Engineers, 2nd Ed. 1986, Sections 18.7 Beats: Interference in Time, pp. 397-400 and 43.7 Semiconductor Devices, Sub-section the diode as a Rectifier, pp. 1027 and 1031.*
Pethig, R.; Talary, M. S.; Lee R. S. Enhancing Traveling-Wave Dielectrophoresis with Signal Superposition, IEEE Eng. Med. Biol. Mag. 2003, vol. 22, pp. 43-50.*

* cited by examiner

*Primary Examiner* — Alex Noguerola
*Assistant Examiner* — Gurpreet Kaur
(74) *Attorney, Agent, or Firm* — Finnegan, Henderson, Farabow, Garrett & Dunner, L.L.P.

(57) ABSTRACT

Disclosed herein is a system for detecting interaction between substances includes a reaction field for allowing the interaction to proceed between the substances, and a voltage application section for applying a voltage to a working electrode arranged facing the reaction field such that a predetermined electrodynamic effect is given to the reaction field. The voltage application section is provided with a section for superimposingly applying two sinusoidal voltages of different frequencies to generate a beat. Also disclosed herein is a method for detecting interaction between substances in a procedure of allowing the interaction to proceed between the substances by making use of a predetermined electrodynamic effect, the method includes the step of applying two sinusoidal voltages of different frequencies superimposingly to generate a beat such that an electrochemical reaction is suppressed in a reaction field where the interaction is allowed to proceed.

4 Claims, 4 Drawing Sheets

SYSTEM AND METHOD FOR DETECTING INTERACTION BETWEEN SUBSTANCES BY SUPERIMPOSINGLY APPLYING SINUSOIDAL VOLTAGE

CROSS REFERENCES TO RELATED APPLICATIONS

The present invention contains subject matter related to Japanese Patent Application JP 2005-102121 filed in the Japanese Patent Office on Mar. 31, 2005, the entire contents of which being incorporated herein by reference.

BACKGROUND OF THE INVENTION

This invention relates to a technology for detecting interaction between substances, and more specifically to a technique for detecting interaction between substances while making use of an electrodynamic effect to eliminate adverse effects of an electrochemical reaction.

In recent years, integrated bioassay plates holding thereon predetermined DNAs microarrayed by microarray technologies and generally called "DNA chips" or "DNA microarrays" (hereinafter collectively called "DNA chips") have been developed, and are finding utility in gene mutation analyses, SNPs (single-base polymorphisms) analyses, gene expression frequency analyses, gene network analyses, and the like. In addition, they are expected to find broad applications in drug developments, clinical diagnoses, pharmacogenomics, tailor-made remedies, research on evolution, forensic medicine, and other fields.

Sensor chip technologies represented by such DNA chips and protein chips with proteins integrated thereon quantitate the existing amounts of target substances by making use of specific interactions between detecting substances (which are often called "probes") immobilized on solid-phase plates and the target substances.

Taking a DNA chip as an example, single-stranded DNA fragments having a segment of the DNA sequence of a target to be analyzed are immobilized beforehand. If DNA molecules having a sequence complementary to the DNA fragments exist in a sample, the DNA fragments and the DNA molecules specifically combine together (in other words, hybridize with each other) to form double-stranded DNA. Relying upon the detection of this double-stranded DNA by a fluorescence labeling technique or the like, a determination is made as to whether or not the DNA molecules have been expressed in the sample solution. Immobilization of numerous single-stranded DNA fragments of different DNA sequences makes it possible to efficiently perform an analysis as to whether or not plural kinds of DNAs have been expressed or to provide an analysis of expression of a single kind of DNA with redundancy such that the accuracy of the analysis is increased.

However, such sensor chips as described above rely upon natural interaction between biomacromolecules so that the reaction rate is determined by a reaction rate constant which is in turn determined by the step of a transport by diffusion and the interaction. Accordingly, the accuracy of the reaction is determined by the equilibrium constant of the interaction. If a sample contains not only true target molecules but also noise molecules having a similar level of affinity to a detecting substance as the true target molecules, these noise molecules are bound to some extent to the detecting substance, leading to a reduction in the accuracy of an analysis by the sensor chip.

With a view to solving this problem, several approaches have been proposed. For example, there are techniques which make use of an electrodynamic effect. Reference will hereinafter be made to related art techniques, which can be placed as constituting a general technical standard in relation to the present invention. Firstly, JP-A-2004-524823 discloses a technique for amplifying an mRNA transcript from a biological sample to obtain amplicons and electrically hybridizing the amplicons to a probe bound (immobilized) at predetermined locations of a support.

To remove molecules other than true target molecules, these former molecules having undesirably hybridized with a ligand in interaction between biomacromolecules (in this case, a hybridization reaction between DNAs), JP-A-2002-541823 proposes a method for applying a direct voltage, which has a polarity opposite to a voltage applied for the improvement of a transporting step, after the interaction between the biomacromolecules (i.e., the hybridization reaction between the DNAs).

Further, JP-A-2004-135512 proposes to improve the efficiency of hybridization by applying a high-frequency alternating-current voltage or the like to induce polarization of nucleotide chains such that they are caused to migrate (dielectrophoresis) in a non-uniform electric field.

SUMMARY OF THE INVENTION

A system in which an application of a voltage to a reaction field is conducted to obtain a predetermined or desired electrodynamic effect involves problems or concerns such as an inhibition to interaction between substances by gas (for example, hydrogen, oxygen, chlorine and/or like) given off from electrochemical reactions on the surfaces of electrodes, separation of a substance immobilized on the surface of the working electrode, and dissolution of the electrodes themselves. As various limitations are imposed on the application of a voltage to the reaction field as described above, it has been difficult to sufficiently obtain the effects as intended on the basis of the electrodynamic effect.

For the prevention of electrochemical reactions on the surfaces of electrodes, it is considered to be effective to form insulating layers with a material such as $SiO_2$, SiC, SiN, SiOC, SiOF or $TiO_2$ on the surfaces of the electrodes. With such a countermeasure, however, an applied voltage drops at the insulating layers, thereby developing another problem that an intended voltage cannot be inputted to a reaction solution.

Therefore, it is desirable to provide a technique that makes it possible to perform the application of a voltage as desired to obtain an intended electrodynamic effect at a reaction field where interaction between substances are allowed to proceed.

In a first aspect of the present invention, there is thus provided a system for detecting interaction between substances, including an reaction field for allowing the interaction to proceed between the substances, and a voltage application section for applying a voltage to a working electrode arranged facing the reaction field such that a predetermined electrodynamic effect is given to the reaction field, wherein the voltage application section is provided with a section for superimposingly applying two sinusoidal voltages of different frequencies to generate a beat. For example, the voltage application section in the system may make use of an electric circuit, which by half-wave rectification, can alternately cut off positive and negative polarities in consecutive half cycles of the beat.

As a result of the adoption of the voltage application section as described above in the present invention, the problem of a voltage drop at the insulating layer does not arise. Despite the construction that the working electrode is covered with the insulating layer, it is, therefore, possible to avoid an electrochemical reaction at the surface of the working electrode as desired while assuring the intended electrodynamic effect based on the voltage applied. The present invention also makes it possible to adopt the construction of immobilizing one of the substances, which take part in the interaction, on the working electrode as desired because any electrochemical reaction on the surface of the working electrode can be effectively prevented.

In a second aspect of the present invention, there is also provided a method for detecting interaction between substances in a procedure of allowing the interaction to proceed between the substances by making use of a predetermined electrodynamic effect, which includes the step of applying two sinusoidal voltages of different frequencies superimposingly to generate a beat such that an electrochemical reaction is suppressed in a reaction field where the interaction is allowed to proceed.

It is to be noted that the term "interaction between substances" as used herein broadly encompasses chemical bondings between substances, including non-covalent bonding, covalent bonding and hydrogen bonding, and chemical dissociations of such bondings. Accordingly, the present invention can be applied to chemical bondings or dissociations between substances, for example, hybridization between nucleic acid molecules, interaction between proteins, antigen-antibody reactions, interaction between low MW molecules and high MW molecules, and so on. It is also to be noted that the term "hybridization" as used herein means a reaction to form a complementary chain (double-stranded) between single-stranded DNA fragments equipped with complementary base-sequence structures.

Further, the term "half-wave rectification" means a rectification method that cuts off one of polarities of an alternating current. In the present invention, half-wave rectification is used as a suitable method upon alternately cutting off positive and negative polarities in the consecutive half cycles of a beat.

According to the present invention, it is possible to avoid any unnecessary electrochemical reaction (the production of hydrogen, oxygen, chlorine and/or the like) on the surface of the working electrode arranged facing the reaction field and, therefore, to freely apply a desired voltage. Even in the form that the working electrode is protected with an insulating layer, the desired voltage can still be applied to a reaction solution without the occurrence of a voltage drop at the insulating layer so that the intended electrodynamic effect can be surely brought about.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

A basic experiment relating to the present invention and examples of the present invention will hereinafter be described with reference to the accompanying drawings. It is, however, to be noted that the present invention shall not be narrowly interpreted by the examples to be described subsequently herein.

Figure 1:
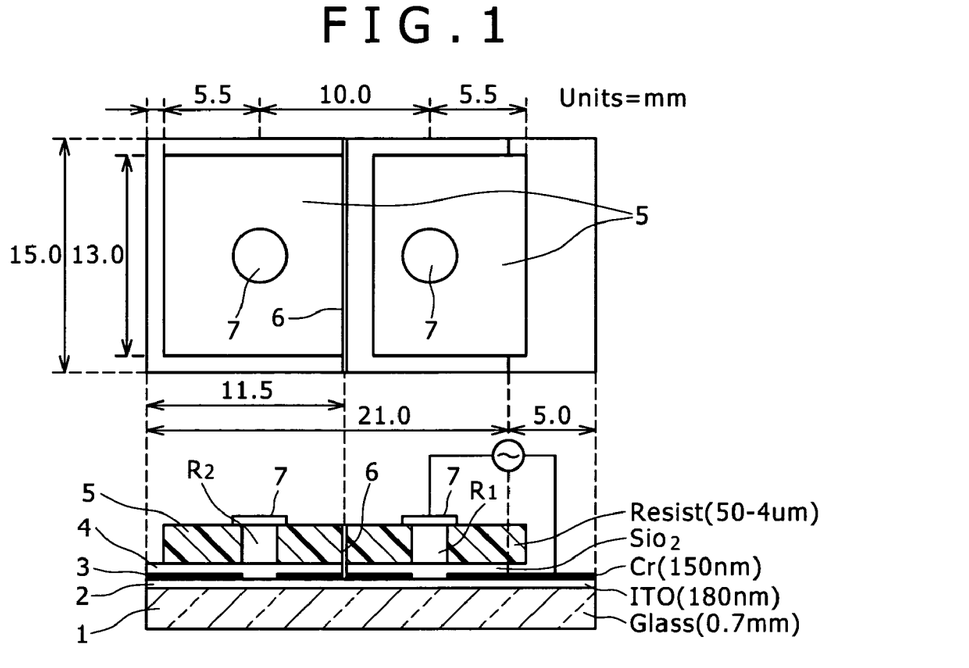
FIG. 1 illustrates the construction of a simulated sensor chip used in a basic experiment (top: plan view, bottom: vertical cross-sectional view)

The basic experiment was conducted using a simulated sensor chip of such a construction as shown in FIG. 1. A base substrate 1 was formed of a glass substrate of 0.7 mm in thickness. On the base substrate 1, a light-transmitting, conductive ITO (indium-tin-oxide) layer 2 was formed to a thickness of 180 nm. This ITO layer 2 was used as a working electrode.

On the ITO layer 2, a light-shielding chromium film 3 for fluorescent microscopic observations was formed such that reaction fields $R_1$, $R_2$ were avoided. Over the light-shielding chromium film 3, silicon dioxide ($SiO_2$) was stacked as a protecting film 4 by sputtering.

As a top layer 5 on the protecting film 4, a photosensitive polyimide resin was applied as a photoresist, and was then exposed to high energy light or the like via a photomask such that the two reaction fields $R_1$, $R_2$ were defined each in a cylindrical form (inner diameter, 2 mm; thickness (depth), 5 µm). It is to be note that one of the reaction fields, the reaction field $R_1$ was used as a reaction field to determine an electrodynamic effect while the other reaction field $R_2$ was employed as a control reaction field.

It is to be noted that the reaction fields $R_1$, $R_2$ are both mounted on the same substrate and will have the same heat history but they are electrically isolated completely from each other owing to the arrangement of a gap 6 at the middle between the reaction fields $R_1$, $R_2$.

On the substrate shown in FIG. 1, diamond-like carbon was firstly formed into a film of about 10 nm in thickness by ion evaporation. Using thermions generated at a tungsten filament, benzene or methane as a feed gas was ionized, and under a bias voltage, was formed into a film on the substrate. Chlorine gas was then introduced into the reaction vessel, and light was irradiated for 30 minutes from a high-pressure mercury vapor lamp.

After chlorine gas was evacuated, ammonia gas was introduced into the vessel, followed by irradiation of light for about 30 minutes from the high-pressure mercury vapor lamp. As a result, amino groups —$NH_2$ were introduced onto the surface. The substrate was then immersed in a solution (pH 8) of succinic anhydride (140 mM) and sodium borate (0.1 M) in 1-methyl-2-pyrrolidone. As a result, carboxyl groups —COOH were introduced onto the surface. Those —COOH groups were then converted into an active ester as will be described hereinafter. A solution of N-ethyl-N'-3-dimethylaminopropylcarbodiimide hydrochloride (0.1 M) and N-hydroxysuccinimide (20 nM) in 0.1 M phosphate buffer was prepared. The above-prepared substrate was immersed for 30 minutes in the solution.

Single-stranded DNA fragments were immobilized on the above-treated surface of the substrate. Those fragments had the following sequence in the direction of from the 5end to the 3end: CGAAGCGCTTATTCCAGAGCCCGACATGAA (30 mer in total). A synthesized oligo having the above-described sequence and terminated at the 5'end thereof with $NH_2$ was purchased from ESPEC OLIGO SERVICE CORP., and was dissolved in pure water to give a concentration of 100 µM. To a 10-µL aliquot of the resulting solution, a solution ("SOLUTION 6", trade name; product of Toyo Kohan Co., Ltd.; 90 µL) so that a 10 µM DNA solution was prepared. Using an automated spotting device ("STAMPMAN", trademark; manufactured by Nippon Laser & Electronics Lab. Co., Ltd.), the DNA solution was spotted to central parts of the two reaction fields $R_1$, $R_2$.

Chips spotted as described above were placed side by side on a glass petri dish, and were then heated at 80° C. for 1 hour in an oven. In the course of that heating, the $NH_2$ terminals of the DNA fragments and the activated ester on the surface reacted so that the DNA fragments were immobilized on the surface.

Each chip was next taken out of the oven. A washing solution (2× standard sodium citrate (SSC)/0.2 Denhardt's solution (DS), 150 mL) was placed in a 500-mL beaker, and the chip was dipped in the washing solution and was washed for 15 minutes with shaking at 100 rpm. In an inactivating solution (2×SSC) prepared in advance and controlled at 90° C., the thus-washed chip was immersed for 5 minutes such that the surplus activated ester which had not reacted with the $NH_2$ terminals of the DNA fragments was inactivated. Subsequently, the chip was rinsed a little in running pure water, and blow-dried with dry nitrogen gas. The chips completed as described above were stored in a nitrogen gas box.

Subsequently, a single-stranded DNA having a sequence completely complementary to the DNA fragments immobilized on the chip and another single-stranded DNA with non-complementary bases artificially inserted therein (also purchased from ESPEC OLIGO SERVICE CORP.) were dissolved at a concentration of 100 µM each in pure water, and further, were adjusted to a concentration of 50 nM in 5×SSC/0.5DS. The 5'ends of the DNA fragments were fluorescently labeled with a fluorochrome Cy3.

The solution was collected in a high-precision pipette, and was added dropwise to the two reaction fields $R_1$, $R_2$ of each chip. The amount of the solution so dropped was 1.5 µL per reaction field. Subsequently, upper electrodes (reference electrodes) 7,7 made of highly-doped silicon were placed over the respective reaction fields $R_1$, $R_2$, and the chip was mounted on a hybridization system equipped with a heating stage. It is to be noted that the system was designed to hold the upper electrodes with pins, respectively, to permit applying a voltage between the working electrode and the reference electrode on only one of the reaction fields.

Using the system, the hybridization was allowed to proceed at 65° C. for varied time periods. Subsequent to the reaction, each chip was washed for 15 minutes with shaking at 100 rpm in 2×SSC/0.2DS. The chip was then blow-dried with dry nitrogen gas, and the extent of the hybridization reaction was measured by a fluorescence microscope ("DP70", trade name; manufactured by Olympus Corporation).

Figure 2:
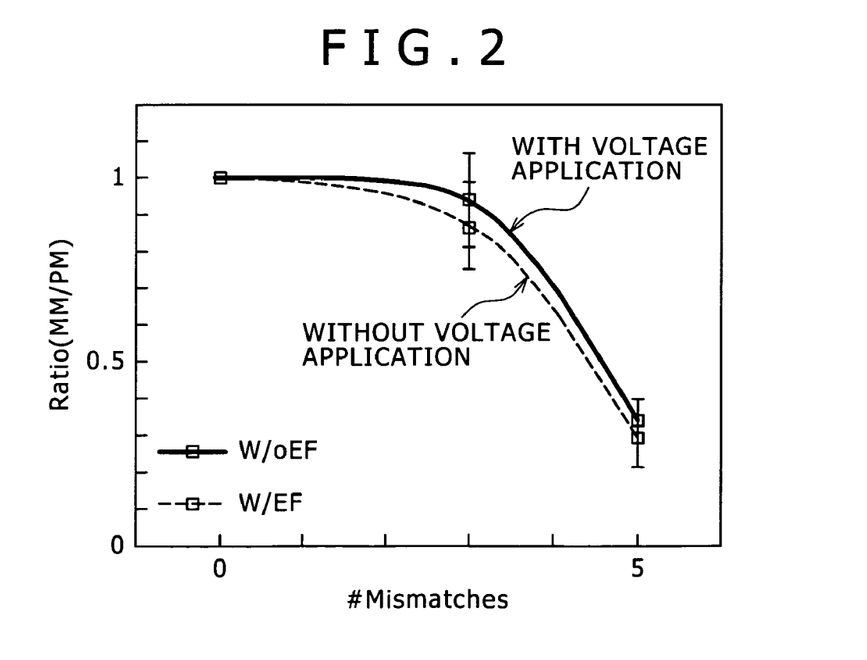
FIG. 2 is a graph showing a comparison in the accuracy of hybridization between a reaction field ($R_1$) with voltage application and another reaction field ($R_2$) without voltage application.

Reference to FIG. 2, the number of non-complementary base groups is plotted along the abscissa and the extent of the hybridization reaction is plotted along the ordinate. It is to be noted that a chip on which the extent of a hybridization reaction abruptly decreases as the number of non-complementary base groups increases is considered to be a high-accuracy chip.

The voltage applied in that experiment was an alternating voltage of 15 Vpp and 5 MHz. As illustrated in FIG. 2, it was ascertained that the accuracy of the hybridization reaction was not different much between the reaction field $R_2$ to which the voltage was applied and the reaction field $R_1$ to which the voltage was not applied. From this, it has been found that the voltage is not effectively inputted to the reaction field $R_1$ by such a chip sensor construction as adopted in this experiment.

Figure 3:
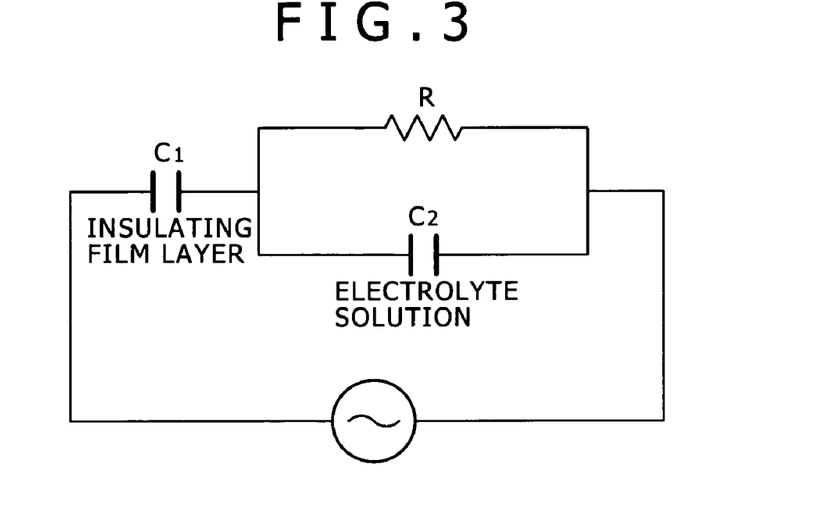
FIG. 3 is a diagram showing an equivalent electric circuit of a system with which the basic experiment was conducted.

Referring next to FIG. 3, a description will be made about the equivalent electric circuit of the system with which the basic experiment was conducted. The electrostatic capacity $C_1$ of the protecting film 4 (in this experiment, the $SiO_2$ film formed by sputtering) in the form of the insulating layer formed on the working electrode (ITO layer 2) is connected in series with a parallel combination of the electrostatic capacity $C_2$ of the solution in the reaction field $R_1$ and a resistance R.

If the frequency of a high-frequency wave to be applied is low in such an electric circuit system, the voltage is applied in its entirety to the protecting film 4 so that the voltage is lowered and hence, not applied to the solution. In other words, the protecting film 4 exhibits a similar function as a capacitor connected in series with the solvent (electrolyte solution) in the reaction field $R_1$, thereby developing a problem that a dc or low-frequency alternating-current voltage is applied to the protecting film 4 on the surface of the working electrode (ITO layer 2) and hence, is not applied to the target reaction solution (which exists in the reaction field).

It is to be noted that the voltage is begun to be applied to the solution when the frequency becomes high and exceeds a threshold and the electric circuit system is brought into such a state as the electrostatic capacity $C_1$ is practically short-circuited. Where a desired electrodynamic effect such as electrophoresis or dielectrophoresis can be exhibited to its maximum at a frequency equal to or lower than the threshold, however, the electrodynamic effect cannot be used efficiently.

Figure 4:
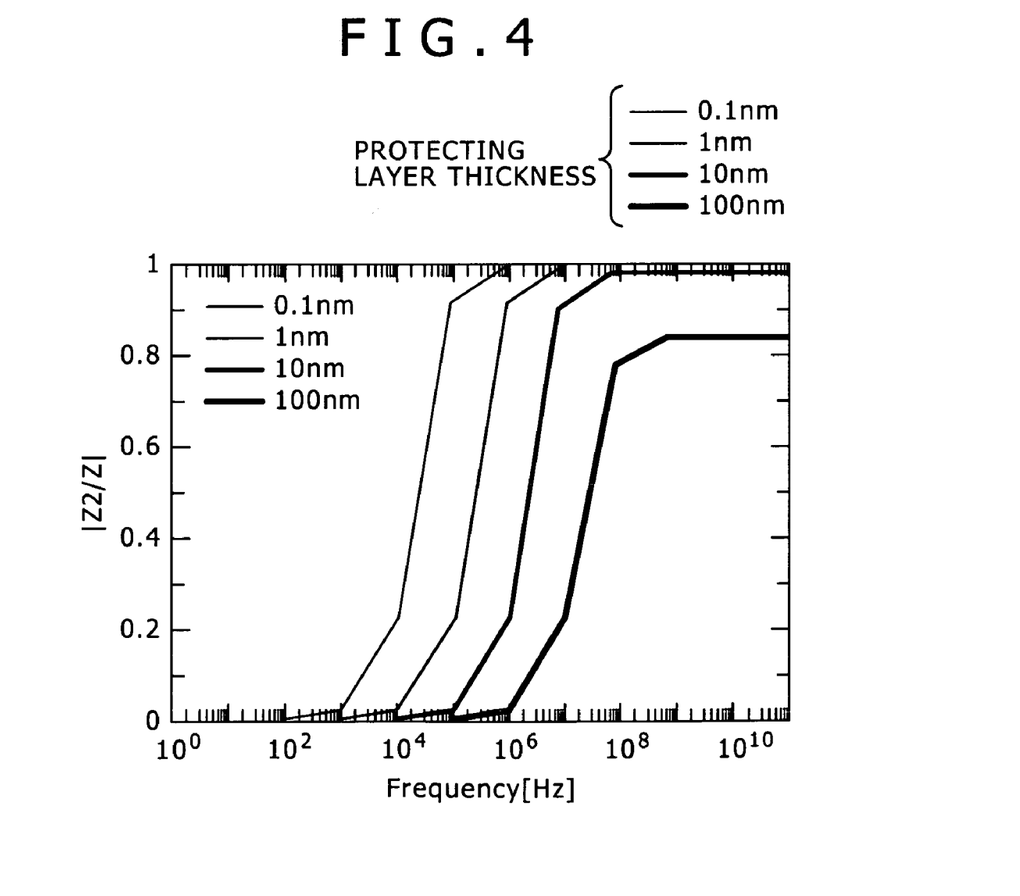
FIG. 4 is a graph showing the ratio of the impedance of a solution portion of the simulated sensor chip illustrated in FIG. 1 to that of the whole circuit as a function of frequency.

Reference is next had to FIG. 4, which is a graph showing the ratio of the impedance of a solution portion of the simulated sensor chip illustrated in FIG. 1 to that of the whole circuit as a function of frequency (frequencies Hz are plotted along the abscissa).

A voltage to be applied to the solution is expressed by the product of a voltage, which is to be inputted to the circuit, multiplied by the ratio of the impedance of the solution to the impedance of the whole circuit. It is to be noted that the diameter and depth of the reaction field $R_1$ were 2 mm and 10 µm, respectively, (as mentioned above) and the reaction field $R_1$ was filled with a 100 mM solution of NaCl. As is evident from the results shown in FIG. 4, it is understood that a voltage cannot be efficiently applied to the solution portion unless an alternating-current voltage of higher frequency is applied as the protecting film 4 becomes thicker.

According to the conventional way of conception, it has been possible to adopt an approach that the thickness of the protecting film 4 is reduced when the use of a low-frequency voltage is desired. There is, however, a (lower) limitation imposed on the thickness of a protecting film insofar as it has to be formed with predetermined quality (insulating property). In FIG. 4, data of a protecting film of 0.1 nm in thickness are also plotted. Needless to say, however, it is practically difficult to form an $SiO_2$ film of such a small thickness.

As a conclusion, the cause of the failure in obtaining any significant electrodynamic effect is considered, as indicated by the results of FIG. 2, to reside in that no voltage was applied to the solution portion because of the excessively large thickness of the protecting film (insulating $SiO_2$ layer).

With the results of the basic experiment and the discussion thereon in view, a description will hereinafter be made of examples relating to the present invention.

Firstly, in a sensor chip such as a DNA chip that is designed to make use of any electrodynamic effect, its optimal frequency differs depending on the kind of the electrodynamic effect intended to be used. In examples to be described hereinafter, a description will be made of the detection of interaction between biomacromolecules by use of "dielectrophoresis" as representative examples. It is, however, to be noted that the electrodynamic effect in the present invention is not limited to dielectrophoresis and may be another electrodynamic effect such as electrophoresis.

In passing, "electrophoresis" means a phenomenon that molecules are driven toward a position higher in electrical field in a system where the electrical field is not uniform. An application of an alternating-current voltage can also bring about similar drive effect as in the case of a dc voltage, because the polarity of polarization also reverses as the polarity of the applied voltage reverses (see, HAYASHI, Teru, Supervisor: "Micromachine and Material Technologies", Chapter 5, Cell and DNA Manupulations, published in Japanese, 37-46, CMC, December, 1999.

To use dielectrophoresis, it is firstly needed to induce polarization in molecules by an electric field (dielectrophoresis) except that the molecules to be subjected to electrophoresis have already been polarized and have sufficiently large permanent dipoles.

It is to be note that nucleic acid molecules are known to extend or move when they are subjected to the action of an electric field in a liquid phase. As the principle of this phenomenon, an ion cloud is considered to be formed by phosphoric ions (negative charges), which make up the skeleton of a nucleic acid molecule, and their surrounding hydrogen atoms (positive charges) derived from water. Polarization vectors (dipoles) produced by these negative charges and positive charges are oriented in one direction as a whole upon application of a high-frequency high voltage, and as a result, each molecule extends. In addition, when a non-uniform electric field that electric lines of force concentrate on a position is applied, the molecules move toward the position on which the electric lines of force concentrate. (SUZUKI Seiichi, YAMANASHI Takeshi, TAZAWA Shin-ichi, KUROSAWA Osamu, and WASHIZU Masao: "Quantitative Analysis on Electrostatic Orientation of DNA in Stationary AC Electric Field Using Florescence Anisotropy", IEEE Transaction on Industrial Applications, 34(1), 75-83 (1998)).

Figure 5:
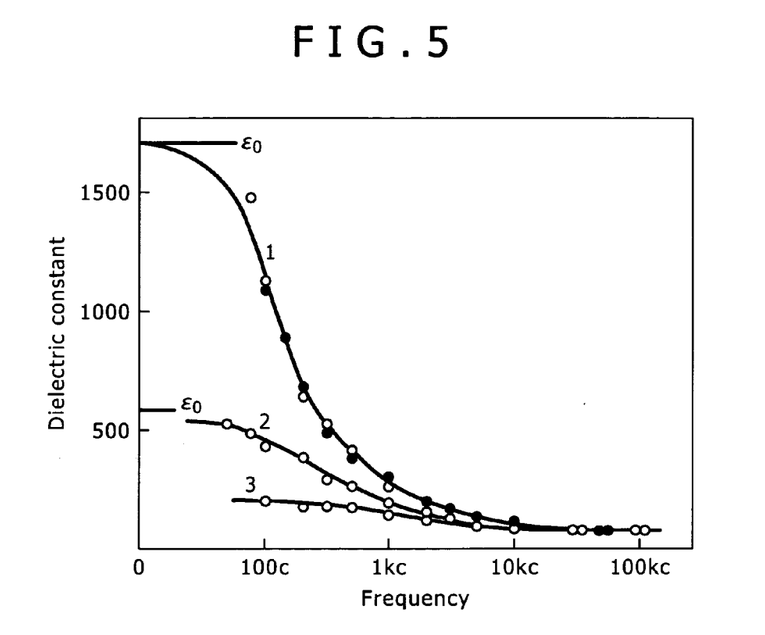
FIG. 5 is a graph illustrating dielectric dispersion (the frequency dependency of dielectric constant) of double-stranded DNA to show around what level of frequency the polarization of DNA takes place.

To firstly determine at which level of frequency the polarization of DNA takes place, the dielectric dispersion (the frequency dependency of dielectric constant) of double-stranded DNA is shown in FIG. 5. It is meant that the greater the ordinate value, the greater the induced polarization. In FIG. 5, the plots indicate the dielectric dispersion of DNA samples extracted from salmon sperms, and the curves 1, 2 and 3 correspond to samples of 740, 560, and 130 nm in strand length, respectively.

From a detailed analysis of the data, it is understood that the frequency at which the dielectric polarization of DNA takes place scales up in proportion to the square of the length of a strand. In other words, polarization takes place at a lower frequency as the strand becomes shorter, and polarization takes place at a higher frequency as the strand becomes longer.

Relying upon this scaling rule, it is appreciated that double-stranded DNA formed of 30 base pairs polarizes at about 10 MHz. With the test chip and electric circuit adopted in the above-described basic experiment, however, alternating-current voltages not higher than about 100 MHz cannot be used. The present invention is effective for meeting these mutually-exclusive requirements.

Figure 6:
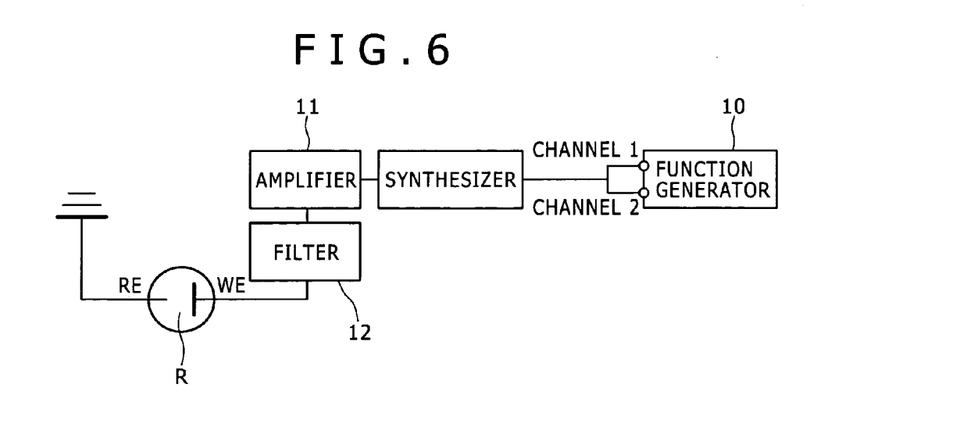
FIG. 6 is an electric circuit diagram usable in the present invention, and the electric circuit diagram has the construction that sinusoidal waves the frequencies of which are close to each other are generated from a two-channel function generator, synthesized together, amplified at an amplifier, and then applied to a chip via a half-wave rectifier filter.

Upon applying a voltage to a reaction field, it is a common practice to generate a sinusoidal wave from a single function generator, to amplify it at an amplifier, and then to apply the thus-amplified wave to the chip. With the voltage application section in the present invention, on the other hand, it is contrived as illustrated in FIG. 6. Described specifically, a two-channel function generator 10 is caused to generate two sinusoidal waves the frequencies of which are close to each other, and subsequent to their synthesis at the synthesizer, the resulting synthesized wave is amplified at an amplifier 11. Via a half-wave rectifier filter 12, the thus-amplified wave is then applied to a reaction field R on the chip. It is to be noted that in FIG. 6, "RE" stands for a working electrode in a vicinity of which interaction is allowed to proceed and "RE" stands for a reference electrode arranged opposite the working electrode.

Now assume that these two frequencies $\omega_1$, $\omega_2$ ($\omega_1 > \omega_2$) are higher than the threshold frequency of the equivalent circuit illustrated in FIG. 3. Also assume that the difference of these two frequencies, $(\omega_1 - \omega_2)$, is equal to the double of a frequency the application of which is actually desired.

When the two sinusoidal waves the frequencies of which are close to each other are synthesized, a beat is generated as a result of modulation of a high-frequency voltage of an average frequency, which is expressed by the following equation 1, by the difference $(\omega_1 - \omega_2)$ in frequency.

$$(\omega_1+\omega_2)/2 \approx \omega_1 \approx \omega_2 \qquad (1)$$

This beat can be expressed by the following equation 2:

$$V = A\sin(\omega_1 t + \phi) + A\sin(\omega_2 t) \qquad (2)$$
$$= 2A\sin\left(\frac{\omega_1 + \omega_2}{2}t + \frac{\phi}{2}\right)\cos\left(\frac{\omega_1 - \omega_2}{2}t + \frac{\phi}{2}\right).$$

where $\phi$ means a phase difference between the wave from the channel 1 and the wave from the channel 2.

As this waveform is oscillating at a frequency $(\omega_1 + \omega_2)/2$ (see the first sine term), the frequency is sufficient by high so that the beat penetrates through the protecting film (insulating layer) and is applied to the solution portion. As understood from the results of the dielectric dispersion shown in FIG. 5, however, no dielectric polarization of DNA is induced if the frequency is excessively high. This means that this high frequency component gives no electrodynamic effect to DNA molecules (in other words, the frequency is so high that the DNA molecules "do not sense the electrical field").

On the other hand, the amplitude of the high-frequency component has been modulated by the frequency $(\omega_1 - \omega_2)/2$ (see the second cosine term). As this modulated frequency is equal to the desired frequency, a low-frequency voltage is applied to the DNA molecules as a practical effect.

Actually, however, the sine term oscillates in a range of from −1 to +1 during a half cycle of the beat. It is, therefore, necessary to cut off the negative components of the high frequency when the cosine term is positive and to cut off the negative components of the high frequency when the cosine term is negative. In a simplest embodiment, the half-wave rectification of this alternating current can be practiced by inserting a diode in the circuit. A diode allows a current to flow only in one direction, and therefore, can perform half-wave rectification.

In the present invention, however, it is necessary to alternately cut off positive and negative polarities in consecutive half cycles of the beat. A variety of electric circuits can be contemplated to realize this half-wave rectification. For example, the intended waveform can be obtained by forming a filter circuit with two diodes of opposite polarities connected in parallel with each other and switching these diodes in synchronization with the half cycles of the beat.

Figure 7:
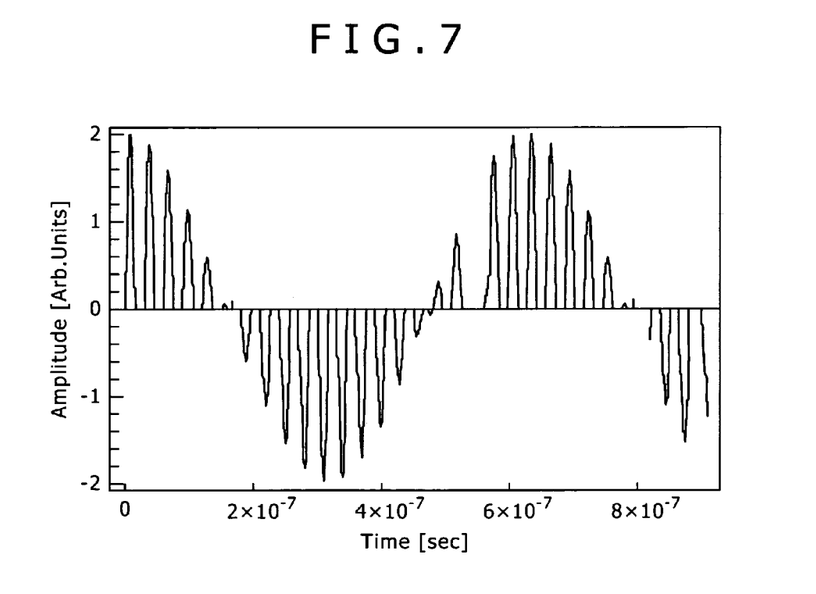
FIG. 7 is a diagram showing the waveform of a superimposing alternating-current voltage applied based on the circuit design of FIG. 6 as observed by an oscilloscope.

Based on the data of FIG. 5 and the scaling rule derived from the data, a superimposing alternating-current voltage was applied on the basis of the circuit design of FIG. 6 while assuming $\omega_1=220$ MHz and $\omega_2=200$ MHz. A waveform as observed on an oscilloscope is reproduced in FIG. 7.

It is to be noted that, as the frequency is higher than 200 MHz, a voltage is applied to the microchip as appreciated from FIG. 4. In the present invention, a high-frequency voltage having a frequency of 210 MHz is modulated at a frequency of 10 MHz.

Nucleic acid molecules such as DNA molecules are considered to dielectrically polarize at the frequency of 10 MHz, so that an effect for the dielectric polarization of nucleic acid molecules can be sufficiently expected in the present invention. The application of the present invention, therefore, makes it possible to apply a voltage of a desired frequency to a microchip such as a DNA chip and to bring about a dielectrophoretic effect even when a protecting film is formed on the surface of a working electrode.

A description will now be made about the penetrability of an alternating current, one of the polarities of which has been cut off, through a protecting film (insulating layer).

Assuming that the impedances of the insulating layer and solution are $Z_1$ and $Z_2$, respectively, the applied voltage V is divided to the ratio of the impedances in every case as indicated by the following equation 3:

$$V_2 = \frac{Z_2}{Z}V, \quad Z = Z_1 + Z_2 \quad (3)$$

Next defining by F a computation equivalent to the function of the half-wave rectification filter that cuts off, for example, the negative polarity of the applied alternating current, the voltage applied to the solution subsequent to the rectification can be expressed by the below-described equation 4. The voltage applied to the reaction solution is, therefore, the same as that obtained by half-wave rectifying the original voltage. Accordingly, the alternating current one of the polarities of which has been cut off can penetrate through the protecting film (insulating layer).

$$V_2' = \frac{Z_2}{Z}F[V] = F\left[\frac{Z_2}{Z}V\right] = F[V_2] \quad (4)$$

Next, dielectrophoretic force is proportional to the gradient of the square of an effective value of the alternating current. Upon taking an average of the beat over time, it is sufficient to take an average of only the beat term over time by ignoring the high-frequency component because the high-frequency component is oscillating fast. Since the amplitude of the beat is twice as much as the original high-frequency voltage, the dielectrophoretic force becomes greater as a matter of fact. It is to be noted that, even when an effect other than dielectrophoresis is used, the electric field can be taken as having a double amplitude.

From the above-described results of the experiment and the foregoing discussion on them, the present invention makes it possible to apply a low-frequency voltage to a reaction solution (in a reaction field) irrespective of the construction of the working electrode, especially even when the working electrode is in a form protected with an insulating film. This can obviate the need for applying an excessively high voltage, thereby making it possible to assure the avoidance of the occurrence of an electrochemical reaction on the surface of the working electrode, the dissolution of the working electrode, or the like. As a result, it is possible to improve the efficiency and accuracy of interaction between substances by making use of an electrodynamic effect such as electrophoresis or dielectrophoresis as desired.

The present invention also makes it possible to immobilize one (for example, nucleic acid molecules) of the substances, which take part in the interaction, on the surface of the working electrode without paying attention to the effect of the electrochemical reaction. Moreover, the options for working electrode and protecting film materials are broadened according to the present invention, thereby making it possible to achieve a cost reduction and the facilitation of chip fabrication.

The present invention can be used in the designing and fabrication of reaction fields which allow interaction to proceed between substances, for example, DNA chips, protein chips and other sensor chips. More specifically, the present invention is useful when an electrodynamic effect such as electrophoresis or dielectrophoresis is utilized in reaction fields which allow interaction to proceed between substances.

While a preferred embodiment of the present invention has been described using specific terms, such description is for illustrative purposes only, and it is to be understood that changes and variations may be made without departing from the spirit or scope of the following claims.

What is claimed is:

1. A system for detecting interaction between substances, comprising:
    a reaction field for allowing said interaction to proceed between said substances, said interaction occurring due to the application of a low frequency voltage resulting in a desired electrodynamic effect; and
    a voltage application section for applying a voltage to a working electrode arranged facing said reaction field, the working electrode having an insulating film covering the surface of the working electrode;
    wherein said voltage application section synthesizes two sinusoidal voltages of different frequencies to generate a resultant signal having a low frequency beat, and having a sufficiently high frequency component such that the resultant signal penetrates the insulating film covering the surface of the working electrode, and the beat generated from the two sinusoidal voltages has a resulting beat frequency sufficiently low to cause the desired electrodynamic effect, allowing said interaction to proceed between said substances; and
    wherein said voltage application section uses an electric circuit, which by half-wave rectification alternately cuts off positive and negative polarities in consecutive half cycles of the beat.

2. The system for detecting interaction between substances according to claim 1, wherein one of said substances which take part in said interaction is immobilized on said working electrode.

3. The system for detecting interaction between substances according to claim 1, wherein said electrodynamic effect is an electrophoretic effect or dielectrophoretic effect.

4. A method for detecting interaction between substances in a procedure of allowing said interaction to proceed between said substances by making use of a predetermined electrodynamic effect, the method comprising:

applying, to an insulating film covering a surface of a working electrode, two sinusoidal voltages of different frequencies superimposingly to generate a resultant signal having a low frequency beat such that an electrochemical reaction is suppressed in a reaction field where said interaction is allowed to proceed, and having a sufficiently high frequency component such that the resultant signal penetrates the insulating film covering the surface of the working electrode, and the beat generated from the two sinusoidal voltages has a resulting beat frequency sufficiently low to cause the predetermined electrodynamic effect, allowing said interaction to proceed between said substances; and using an electric circuit, by half-wave rectification, to alternately cut off positive and negative polarities in consecutive half cycles of the beat.

* * * * *